US00PP29332P3

(12) United States Plant Patent
Stemkens

(10) Patent No.: US PP29,332 P3
(45) Date of Patent: May 29, 2018

(54) ***VERBENA* PLANT NAMED 'VEAZ0031'**

(50) Latin Name: *Verbena hybrida*
Varietal Denomination: VEAZ0031

(71) Applicant: SYNGENTA PARTICIPATIONS AG, Basel (CH)

(72) Inventor: Henricus Godefridus Wilhelmus Stemkens, Enkhuizen (NL)

(73) Assignee: Syngenta Participations AG, Basel (CH)

( * ) Notice: Subject to any disclaimer, the term of this patent is extended or adjusted under 35 U.S.C. 154(b) by 0 days. days.

(21) Appl. No.: 15/330,486

(22) Filed: Sep. 27, 2016

(65) Prior Publication Data

US 2017/0150670 P1 May 25, 2017

(30) Foreign Application Priority Data

Nov. 19, 2015 (QZ) ..... PBR 2015/2726

(51) Int. Cl.
*A01H 5/02* (2018.01)

(52) U.S. Cl.
USPC ..... Plt./308

(58) Field of Classification Search
USPC ..... Plt./308
CPC ..... A01H 5/02; A01H 5/00
See application file for complete search history.

(56) References Cited

PUBLICATIONS

Dummen Orange for you Bedding Plants 2015-2016 published on Aug. 9, 2015, retrieved on Oct. 3, 2017, retrieved from the Internet at https://issuu.com/bepplersrl/docs/catalog_d_m-men_orange_2015-2016, pp. 180-181 (Year: 2015).*
Malmborg's Greenhouse Spring 2017 Rooted Cuttings, retrieved on Mar. 1, 2018, retrieved from the Internet at https://issuu.com/erin2350/docs/2017_catalog_online, pp. cover page, 70, 75-78, 80. (Year: 2016).*

* cited by examiner

*Primary Examiner* — June Hwu
(74) *Attorney, Agent, or Firm* — Dale Skalla

(57) ABSTRACT

A new *Verbena* plant named 'VEAZ0031' particularly distinguished by the large sized inflorescences, the flowers with dark red color, dark green, undivided leaves, and a trailing plant habit.

1 Drawing Sheet

Latin name of the genus and species of the plant claimed: *Verbena hybrida.*

Varietal denomination: 'VEAZ0031'.

BACKGROUND OF THE NEW PLANT

The present invention comprises a new *Verbena*, botanically known as *Verbena hybrida*, and hereinafter referred to by the variety name 'VEAZ0031'.

'VEAZ0031' is a product of a planned breeding program. The new cultivar has large sized inflorescences, dark red flowers, dark green, un-divided leaves and a trailing plant habit.

'VEAZ0031' originated from an open pollination made in August 2012 in a greenhouse in Enkhuizen, The Netherlands. The female parent was a plant designated 'P3088-4', having a red flower color with a peach starpattern, and a semi upright plant habit, which later became 'VEAZ0033' (U.S. Plant patent application Ser. No. 15/330,455). The male parent of 'VEAZ0031' is unknown.

The resulting seed was sown in February 2013 in a greenhouse in Enkhuizen, The Netherlands, and 'VEAZ0031' was selected as one flowering plant within the progeny of the stated cross in May 2013.

The first act of asexual reproduction of 'VEAZ0031' was accomplished when stem tip cuttings were propagated in June 2013 in a greenhouse in Enkhuizen, The Netherlands.

BRIEF SUMMARY OF INVENTION

Horticultural examination of plants grown from cuttings of the plant initiated in the fall of 2013, and continuing thereafter, has demonstrated that the combination of characteristics as herein disclosed for 'VEAZ0031' are firmly fixed and are retained through successive generations of asexual reproduction.

'VEAZ0031' has not been observed under all possible environmental conditions. The phenotype may vary significantly with variations in environment such as temperature, light intensity, and day length.

A Plant Breeder's Right for this cultivar was applied for in the European Union (CPVO—Community Plant Variety Office) on Nov. 19, 2015 and assigned application No. 2015/2726.

'VEAZ0031' has not been made publicly available prior to the effective filing date of this application, notwithstanding any disclosure that may have been made less than one year prior to the effective filing date of this application by the inventor or another who obtained 'VEAZ0031' directly from the inventor.

The following traits have been repeatedly observed and are determined to be basic characteristics of the new variety. The combination of these characteristics distinguishes this *Verbena* as a new and distinct variety.

BRIEF DESCRIPTION OF THE PHOTOGRAPHS

The accompanying photographic drawing shows typical flower and foliage characteristics of 'VEAZ0031' with colors being as true as possible with an illustration of this type.

Figure 1:
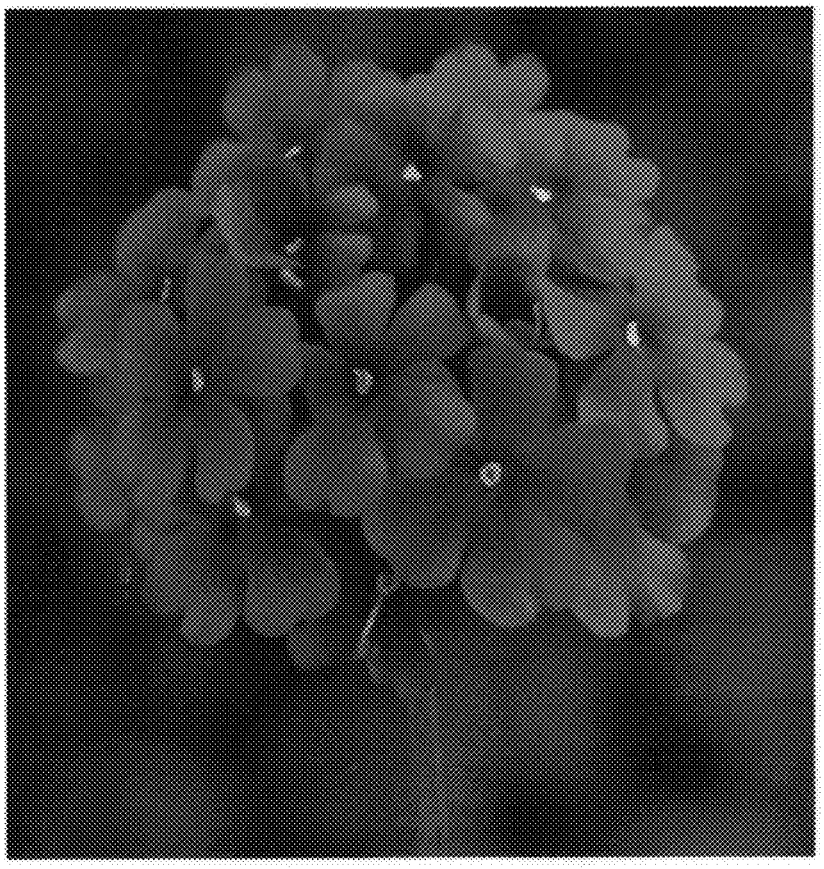
Figure 2:
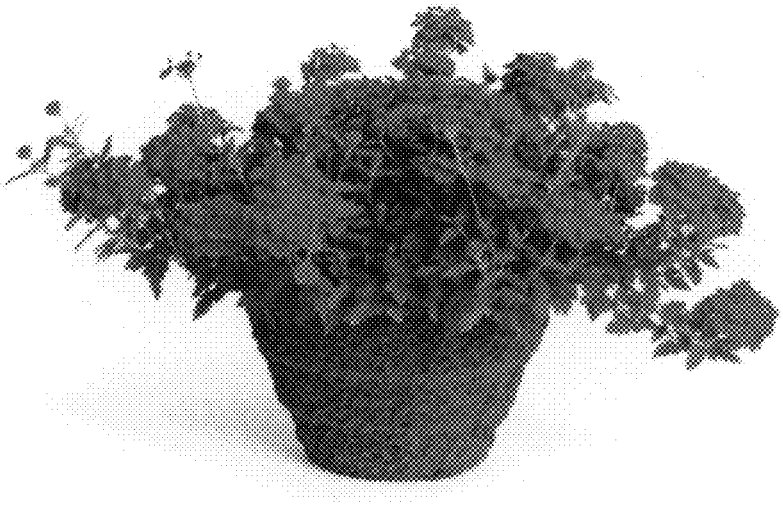

The photographic drawing in FIG. 1 shows a close view of an inflorescence of the new plant and in FIG. 2 a whole flowering plant. The aforementioned photograph was taken in July 2016 in Andijk, The Netherlands. The plants were about 12 weeks old and were grown in 12 cm pots.

DETAILED BOTANICAL DESCRIPTION

Color references are made to The Royal Horticultural Society Colour Chart (R.H.S.) 2001.

TABLE 1

DIFFERENCES BETWEEN THE NEW VARIETY 'VEAZ0031' AND A MOST SIMILAR VARIETY

| | 'VEAZ0031' | 'Empress Cherry Red' |
|---|---|---|
| Flower color: | Dark Red | More cherry red |
| Flower, size: | Smaller | Larger |
| Leaf, size: | Large | Medium |
| Mildew susceptibility: | Not susceptible | Very Susceptible |

Plant:

*Form, growth and habit.*—Herbaceous, trailing and free-branching.
*Plant height.*—17.0 cm.
*Plant height (inflorescence included).*—21.0 cm.
*Plant width.*—47.0 cm.

Roots:

*Number of days to initiate and produce roots.*—11-14 days at about 22 degrees C.
*Type.*—Fine, fibrous, free branching.
*Color.*—RHS N155B but whiter.

Foliage:

*Arrangement.*—Opposite, simple.
*Immature, leaf color, upper surface.*—RHS 138A.
*Immature, leaf color, lower surface.*—RHS 137B.
*Mature, leaf color, upper surface.*—RHS 137A.
*Mature, leaf color, lower surface.*—RHS 137C.
*Length.*—Approximately 3.5 cm.
*Width.*—3.5-4.0 cm.
*Shape.*—Hastate.
*Base shape.*—Obtuse.
*Apex shape.*—Obtuse.
*Margin.*—Entire.
*Texture, upper surface.*—Pubescent.
*Lower surface.*—Pubescent.
*Color of veins, upper surface.*—RHS 145C.
*Color of veins, lower surface.*—RHS 145B.
*Pattern of veining.*—Pinnate.
*Petiole color.*—RHS 145C.
*Petiole length.*—0.6 cm.
*Petiole width.*—0.4 cm.
*Texture.*—Hirsute.

Stem:

*Branching characteristics.*—Side branches develop potentially at each node.
*Quantity of main branches per plant.*—9 to 12.
*Color of stem.*—RHS 143A.
*Stem length.*—About 15.0-24.0 cm.
*Stem width.*—About 0.4 cm.
*Length of internodes.*—About 2.6 to 3 cm.
*Texture.*—Hirsute.
*Color of peduncle.*—RHS 138B.
*Length of peduncle.*—From 2.0 to 3.5 cm.
*Peduncle diameter.*—0.4 cm.
*Texture.*—Canescent, also short, transparent glandular hairs.

Inflorescence:

*Type.*—Umbel-like, but actually a spike, umbrella-shaped.
*Blooming habit.*—Flowers continuously during the summer months.
*Lastingness of individual blooms on the plant.*—About 4-6 days in the greenhouse.
*Fragrance.*—None.
*Number of inflorescences per plant.*—38 at various stages at development.
*Horizontal diameter of inflorescence.*—5.9-6.4 cm.
*Depth of inflorescence.*—3.4 cm.
*Number of florets and buds per inflorescence.*—Approximately 23-29.

Bud:

*Color.*—RHS N155B.
*Length.*—0.5 cm (corolla only).
*Width.*—0.3 cm.
*Shape.*—Tubular with bulbous apex.

Floret:

*Form.*—Sessile; salver-shaped, composed of 5 partly fused petals with a base of a narrow tube.
*Immature color, upper surface.*—RHS 46B.
*Immature color, lower surface.*—RHS 53A.
*Mature color, upper surface.*—RHS 46C.
*Mature color, lower surface.*—RHS 53A.
*Floret diameter.*—3.8 cm.
*Floret length (depth).*—3.2 cm.
*Petal length.*—1.3 cm.
*Petal width.*—1.5 cm.
*Shape.*—Obcordate.
*Apex shape.*—Emarginate.
*Margin.*—Entire.
*Petal texture, upper surface.*—Papillose; pubescent.
*Petal texture, lower surface.*—Papillose, pubescent.
*Corolla tube length.*—2.3 cm.
*Corolla tube width.*—0.3 cm.
*Corolla tube color inside.*—RHS 53A.
*Tube color outside.*—RHS 53B.
*Corolla texture, inside.*—Pubescent.
*Corolla texture, outside.*—Canescent, lower part glabrous.
*Throat hair color.*—RHS 155D but whiter.
*Corolla lobes.*—Free.
*Presence of anthocyanin on the calyx.*—Yes at the base.
*Undulation of the petal.*—Weak.
*Corolla eye.*—No corolla eye.

Calyx:

*Type.*—Five sepals whose margins are fused to each other along their length, with a transparent membrane of less than 0.1 cm in width and with one smaller sepal attached to the base of the calyx.
*Color of sepals.*—RHS 143A.
*Length of sepals.*—1.0 cm.
*Width of sepals.*—0.2 cm.
*Sepal shape.*—Fused, linear.
*Apex shape.*—Acute.
*Margins.*—Entire.

*Texture*.—Densely covered with very short glandular hair.

Reproductive organs:

Gynoecium:

*Pistil*.—1.

*Pistil length*.—1.7 cm.

*Style color*.—RHS N144C.

*Style length*.—1.5 cm.

*Stigma color*.—RHS 144A.

*Ovary color*.—RHS 144B.

*Ovary length*.—0.2 cm.

*Ovary width*.—0.1 cm.

Androecium:

*Stamens*.—Anthers and filaments fused to upper half of corolla tube; four anthers with two pollen sacs per anther.

*Color of filaments*.—RHS 151D.

*Filament length*.—0.2 cm.

*Anther color*.—RHS 151C.

*Anther length*.—0.1 cm.

*Pollen amount*.—None observed.

Fertility/seed set: Neither seed nor fruit production has been observed to date.

Disease/pest resistance: Resistance to pathogens and pests common to *Verbena* has not been observed.

What is claimed is:

1. A new and distinct variety of *Verbena* plant named 'VEAZ0031' substantially as illustrated and described herein.

* * * * *